United States Patent [19]
Tremblay

[11] Patent Number: 5,833,978
[45] Date of Patent: Nov. 10, 1998

[54] METHOD OF IN VITRO PRECONDITIONING HEALTHY DONOR'S MYOBLASTS BEFORE TRANSPLANTATION THEREOF IN COMPATIBLE PATIENTS SUFFERING OF RECESSIVE MYOPATHIES LIKE MUSCULAR DYSTROPHY, FOR IMPROVING TRANSPLANTATION SUCCESS

[75] Inventor: Jacques P. Tremblay, Bernières, Canada

[73] Assignee: Universite Laval, Quebec, Canada

[21] Appl. No.: 404,888

[22] Filed: Mar. 16, 1995

[51] Int. Cl.$^6$ ........................................ C12N 5/06
[52] U.S. Cl. ........................ 424/93.7; 435/366; 435/377
[58] Field of Search ...................... 435/240.2, 240.21, 435/240.3, 240.31, 240.1, 377, 366; 424/93.7, 93.21; 514/2; 604/93

[56] References Cited

U.S. PATENT DOCUMENTS

| | | |
|---|---|---|
| 5,130,141 | 7/1992 | Law et al. . |
| 5,324,656 | 6/1994 | Han et al. ............................. 435/240.2 |
| 5,435,999 | 7/1995 | Austin ....................................... 424/93 |

FOREIGN PATENT DOCUMENTS

WO 91/07992   6/1991   WIPO .

OTHER PUBLICATIONS

Kinoshita et al., Muscle and Nerve 18(8): 834–841 (Aug. 1995).
Wakeford S, et al. (1991). *Muscle and Nerve*. 14: 42–50.
Tremblay JP et al. (1993). *Cell Transplantation*. 2: 99–112.
Vaidya, TB et al. (1989). *Molecular Cellular Biol*. 9(8): 3576–3579.
Vilquin et al. (1994). *Transpl. Proc*. 26(6): 3372–3373.
Sugita H, et al. (1988). *Proc. Japan Acad*. 64: 37–39.
Tienari, J et al. (1994). *Int. J. Cancer*. 56: 219–223.
Tremblay, JP et al. (1993). *Neuromusc. Disord*. 3(5/6): 583–592.
Partridge TA (1991). *Muscle and Nerve*. 14: 197–212.
Partridge TA, et al. (1989). *Nature*. 337: 176–179.
Patte C and Blanquet PR (1992). *Cell. Mol. Biol*. 38: 429–436.
Lowe et al. (1993). *Endocrinology*. 132: 1593–1602.
Morgan JE (1994). *Human Gene Therapy*. 5: 165–173.
Morgan JE et al. (1993). *J. Neurol. Sci*. 115: 191–200.
Koenig M et al. (1987). *Cell*. 50: 509–517.
Labrecque C et al. (1992). *Transplant. Proc*. 24(6): 2889–2892.
Law PK et al. (1990). *Lancet*. 336: 114–115.
Karpati G et al. (1989). *Am. J. Pathol*. 135: 27–32.
Kinoshita I et al. (1994). *Muscle and Nerve*. 17: 975–980.
Kinoshita I et al. (1994). *Muscle and Nerve*. 17: 1407–1415.
Huard J et al. (1992). *Muscle and Nerve*. 15: 550–560.
Huard J et al. (1994). 93: *J. Clin. Invest*. 586–599.
Karpati G et al. (1993). *Ann. Neurol*. 34 (1): 8–17.
Hoffman EP et al. (1987). *Cell*. 51: 919–928.
Hsu H–Y et al. (1994). *J. Biol. Chem*. 269(12): 9213–9220.
Huard J et al. (1994). *Muscle and Nerve. Suppl*. 1: S260.
Grounds MD (1991). *Path. Res. Pract*. 187: 1–22.
Gussoni E, et al. (1992). *Nature*. 356: 435–438.
Hallauer SM et al. (1993). *Development*. 119: 691–701.
DiMario J, et al. (1989). *Science*. 244: 688–690.
DiMario J and Strohman RC (1988). *Differentiation*. 39: 42–49.
Florini, JR and Magri KA (1989). *Am. J. Physiol*. 256: C701–711.
Chen M, et al. (1992). *Cell Transpl*. 1: 17–22.
Clarke MSF, et al. (1993). *J. Cell Sci*. 106: 121–133.
Clegg CH, et al. (1987). *J. Cell Biol*. 105: 949–956.
Beauchamp, JR, et al. (1994). *Muscle and Nerve Supp*. 1: S261.
Bischoff R (1986). *Dev. Biol*. 115: 140–147.
Chen G and Quinn LS. (1992). *J. Cell. Physiol*. 153: 563–574.
Arahata K, et al. (1988). *Nature*. 333: 861–863.
Austin L, et al. (1992). *J. Neurol. Sci*. 112: 185–191.
Austin L and Burgess AW. (1991). *J. Neurol. Sci*. 101: 193–197.
Allen RE and Boxhorn AL. (1989). *J. Cell. Physiol*. 138: 311–315.
Anderson JE, et al. (1993). *Growth Factor* 9: 107–121.
Anderson JE, et al. (1991). *Develop. Biol*. 147: 96–109.
Second International Congress of the Cell Transplant Society, Minneapolis, Minn., USA, May 1–4, 1994, transplantation proceedings 26(6) . 1994. 3518, XP000572288.

*Primary Examiner*—Jean C. Witz
*Attorney, Agent, or Firm*—Griffin, Butler Whisenhunt & Szipl

[57] ABSTRACT

A method of pretreating healthy donor's myoblast cultures with growth or trophic factors like basic fibroblast growth factor (bFGF) on transplantation to subjects suffering of recessive myopathy like muscular dystrophy is disclosed and claimed. Recipient muscles show a higher percentage of functional cells, demonstrated by the higher incidence of dystrophin-positive fibers, and does not require previous preconditioning of recipient muscles by irradiation or toxin administration. Donor mouse myoblasts expressing the reporter gene β- galactosidase were grown with 100 ng/ml bFGF during the last two days before injecting them in the left tibialis anterior (TA) muscles of recipient MHC-compatible mdx mice, an experimental animal model of muscular dystrophy. Myoblasts from the same primary cultures were also grown without bFGF and injected in the right TA muscles as control. The recipient mice were immunosuppressed with FK 506. Twenty-eight days after myoblast transplantation, the percentage of β- galactosidase-positive fibers was significantly higher (more than a 4 fold increase) following culture with bFGF than without bFGF. Almost all β-galactosidase-positive-fibers were also dystrophin positive.

29 Claims, 3 Drawing Sheets

METHOD OF IN VITRO PRECONDITIONING HEALTHY DONOR'S MYOBLASTS BEFORE TRANSPLANTATION THEREOF IN COMPATIBLE PATIENTS SUFFERING OF RECESSIVE MYOPATHIES LIKE MUSCULAR DYSTROPHY, FOR IMPROVING TRANSPLANTATION SUCCESS

FIELD OF THE INVENTION

The present invention is a method for preconditioning healthy donor's myoblasts in vitro before transplantation thereof in compatible patients suffering of recessive myopathies, particularly of muscular dystrophy. This in vitro preconditioning improves the success of the transplantation while not requiring an in vivo preconditioning of the patient's muscle by irradiation or by administering muscular toxin.

BACKGROUND OF THE INVENTION

Duchenne muscular dystrophy (DMD) is a progressive disease characterized by the lack of dystrophin under the sarcolemmal membrane[6,19,28,37]. One possible way to introduce dystrophin in the muscle fibers of the patients to limit the degeneration is to transplant myoblasts obtained from normal subjects[30,34,35]. Several groups have tried myoblast transplantations to DMD patients but poor graft success was observed[17,22,24,38]. Even in experimental myoblast transplantation using mdx mice, an animal model of DMD[10,25,29], large amount of dystrophin-positive fibers were observed only when nude mdx mice were previously irradiated to prevent regeneration of the muscle fibers by host myoblasts[32,43]. High percentage of dystrophin-positive fibers was also observed in mdx mice immunosuppressed with FK 506 and in SCID mice, in both cases muscles were previously damaged by notexin injection and irradiated[23,27]. These results indicate that to obtain successful myoblast transplantation, it is necessary to have not only an immunodeficient mouse or a mouse adequately immunosuppressed but also a host muscle which has been adequately preconditioned. It is, however, impossible in clinical studies to use damaging treatments such as marcaine, notexin and irradiation. If good myoblast transplantation results can be obtained without using such techniques, this would be very helpful for myoblast transplantation in humans.

Recently there has been an increasing interest on the effects of basic fibroblast growth factor (bFGF) and other growth factors on myoblast cultures and myoblast cell lines[1,4,5]. Basic FGF has been reported to both stimulate proliferation and inhibit differentiation of skeletal myoblasts in vitro[15,16]. Other growth or trophic factors like insulin growth factor I, transferrin, platelet-derived growth factor, epidermal growth factor, adrenocorticotrophin and macrophage colony-stimulating factor as well as C kinase proteins activators or agonists by which the effect of bFGF is mediated[20] may also have similar or even better effects than bFGF on the success of myoblast transplantation. The use of these stimulating properties to enhance the success of transplantation by in vitro preconditioning of donor's cells and to replace at least partially the use of previously known methods of in vivo preconditioning of recipients' cells has never been suggested before.

STATEMENT OF THE INVENTION

The present invention relates to a method of in vitro preconditioning of myoblasts harvested from healthy donor's biopsy prior to their transplantation in patients affected by recessive myopathies, particularly by Duchenne muscular dystrophy (DMD). In a DMD animal model (mdx), compatible donor mouse myoblasts were grown in culture with muscular growth or trophic factors, particularly, basic Fibroblast Growth Factor (bFGF), before transplanting them in muscles of mdx mice without any previous damaging treatment. A four fold increase in the percentage of muscle fibers expressing dystrophin, which is indicative of functional muscle cells, was obtained with pretreatment with bFGF. These experimental results are expected to verify in naturally occurring dystrophy or other types of recessive myopathies in animal and human subjects, since the mdx mouse is an animal model wherein muscular dystrophy is naturally occurring.

DESCRIPTION OF THE INVENTION

Although the present trend on research for the treatment of DMD seems to be towards gene therapy, rather than cell therapy, there is still a great deal of work to be done in animal models before either approach, or a mixture of both approaches will be required for the treatment of inherited myopathies such as DMD[32,34].

No satisfactory level of dystrophin expression was obtained following myoblast transplantation not only in clinical trials but also in animal experiments not using irradiation[33] combined with marcaine or notexin destruction of the muscle[26,27]. These techniques are, however, too damaging, too invasive or too risky to be used in clinical trials. Basic FGF has been reported to both stimulate proliferation and inhibit differentiation of skeletal myoblasts by suppressing muscle regulatory factors such as MyoD and myogenin[12,41]. Expression of bFGF has been examined in regenerating skeletal muscles by immunohistochemistry and in situ hybridization, and found to be up-regulated compared to non-injured muscles[3,11]. Increased skeletal muscle mitogens have also been observed in homogenates of regenerating muscles of mdx mice[3]. There are increased levels of bFGF in extracellular matrix of mdx skeletal muscles[13], mdx satellite cells associated with repair[3] and such cells respond more sensitively to exogenous addition of bFGF[14]. There is a high degree of homology between bFGF from various species[2] therefore recombinant human bFGF is active on mouse cells[9]. In the present series of experiments, myoblasts were pretreated with recombinant human bFGF to increase their proliferation and to verify whether such treatment which is less invasive could have beneficial effects on myoblast transplantation.

In our experiments, primary myoblast cultures from the same donors were grown with or without bFGF and transplanted simultaneously to both tibialis anterior (TA) muscles of the same mice. This seems to be a good model to verify the effect of bFGF because the same primary myoblast cultures, the same grafting conditions and the same immunosuppressive state were used. Comparing both TA muscles, in all treated mdx mice, the percentage of β-galactosidase-positive fibers (this enzyme being a reporter gene) were significantly higher in left TA muscles cultures (with bFGF) than in right TA muscles cultures (without bFGF). In the muscles grafted with myoblasts grown with bFGF, the average percentage of hybrid fibers was 34.4%, with two muscles containing over 40% of donor or hybrid fibers. These are the best results ever reported following myoblast transplantation without notexin or irradiation treatment.

In the present study, myoblasts were incubated with bFGF during 48 hours and about 5 millions of these cells (about 1.75 million myogenic cells) were injected in one TA muscle. The same number of myoblasts not incubated with bFGF was injected in the control contralateral TA muscle. The higher percentage of β-galactosidase/dystrophin-positive fibers was therefore not the consequence of a higher proliferation of the myoblasts in vitro before the transplantations.

Our in vitro results indicate that an incubation during 2 days with bFGF did not significantly modify the total number of cells and the percentage of myogenic nuclei. Basic FGF did, however, significantly inhibit the fusion of myoblasts in vitro. This resulted in a small but significant increase (35%) of the percentage of myoblasts among mononuclear cells. This increase seems too small to account alone for the more than four fold increase of effectiveness of myoblast transplantation produced by bFGF. Recently both Partridge[7] and Karpati's[24] group reported that a high percentage (up to 99% in Partridge's results) of the myoblasts injected in a mouse die within 5 days. This dramatic result does not seem attributable to immunological problems since it was observed following autotransplantation[24] or transplantation in nude mice[7]. In our experiments, although there were slightly more cells surviving three days post-transplantation for the cultures treated with bFGF, the difference did not reach a significant level and does not seem to account alone for the 4 fold beneficial effect observed 30 days post transplantation.

Basic FGF is thought to regulate myogenesis during muscle development and regeneration in vivo[3]. The increase percentage of muscle fibers containing the donor gene produced by the addition of bFGF may seem surprising since bFGF was reported to inhibit differentiation of myoblasts in vitro[1,13]. Basic FGF is, however, one of many growth factors which are liberated following muscle damage[7]. These factors, all together, certainly increase myoblast proliferation and eventually muscle repairs. We have also observed that following a two day incubation with bFGF of primary myoblast cultures, myoblast fusion occurred within a few days after removal of bFGF (data not shown). The inhibition by bFGF on myoblast fusion is therefore not irreversible. Basic FGF is already at an increased level in mdx muscle, therefore it is not surprising that direct intra-muscular injection did not increase the fusion of the donor myoblasts with the host fibers. In fact, bFGF injected directly in the muscle probably stimulates the proliferation of the host as well as the donor myoblasts and therefore do not favour the donor myoblasts. On the contrary, preliminary stimulation by bFGF of the donor myoblasts in culture may favour these myoblasts to proliferate more and eventually participate more to muscle regeneration than the host myoblasts. Although bFGF stimulates the fibroblasts, a result which could pose an inconvenience to primary myoblast cultures, the 48 hours incubation of myoblast primary culture with bFGF, did not adversely affect our transplantation results. In fact, to the contrary, it improved them. If primary myoblast cultures were made fibroblast-free by sub-cloning, it would be envisageable to precondition the donors' myoblasts for a longer time, thereby increasing the number of cells to be transplanted from a relatively small biopsy.

Although the results obtained following transplantation of myoblasts grown with bFGF are not as good than those obtained using irradiation and notexin[27], these results are nevertheless important because no technique to destroy the muscles was used. The proposed in vitro preconditioning method might therefore be used in complete replacement of such in vivo damaging pretreatment of recipient cells, or at least in partial replacement thereof, which will result in a substantial diminution of undesirable effects. The effects of many growth factors and trophic factors on myoblast culture have been reported, it is possible that other factors such as insulin growth factor I, transferrin, platelet-derived growth factor, epidermal growth factor, adrenocorticotrophin and macrophage colony-stimulating factor may also have similar or even better effects than bFGF on the success of myoblast transplantation[7]. Furthermore, since the effect of bFGF is mediated by proteins kinase C, pharmacological agents used to enhance the activity of these enzymes (like phorbol esters) or mimicking the effect thereof (agonists) might also be used for preconditioning myoblasts. Therefore, at least one of these factors can be used alone or in combination with or without bFGF to enhance the success of myoblast transplantation. While the mechanism involved remains speculative, bFGF seems to improve the long term viability, multiplication and fusion of myoblasts. Our results suggest that pretreatment of myoblasts with bFGF may be one procedure that may increase the success of myoblast transplantation in DMD patients.

Figure 1A:
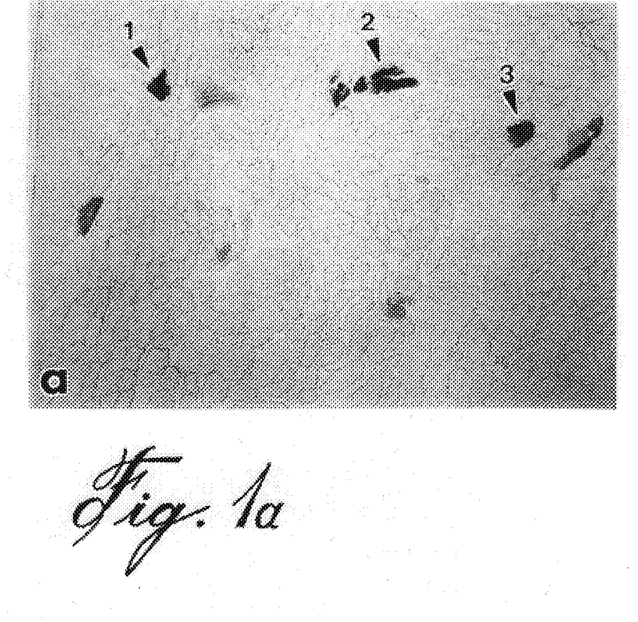
Figure 1B:
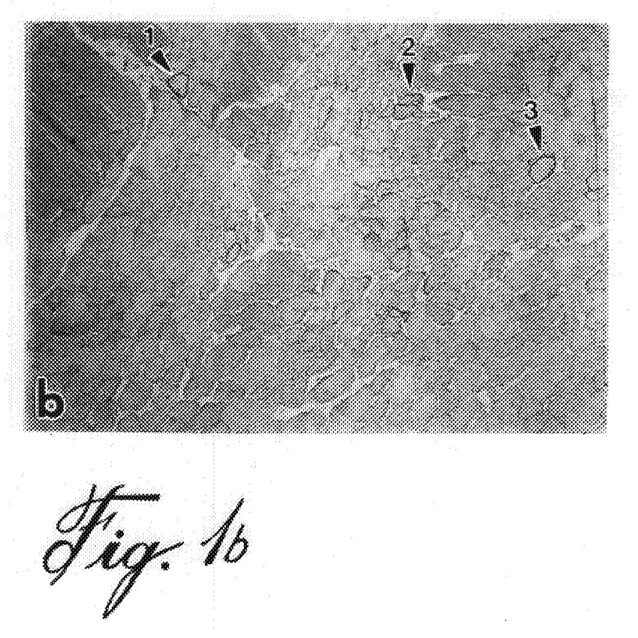
Figure 1C:
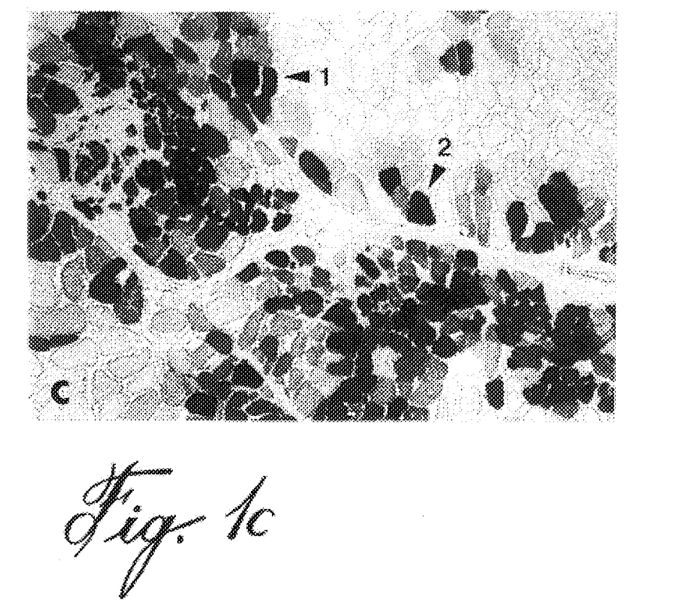
Figure 1D:
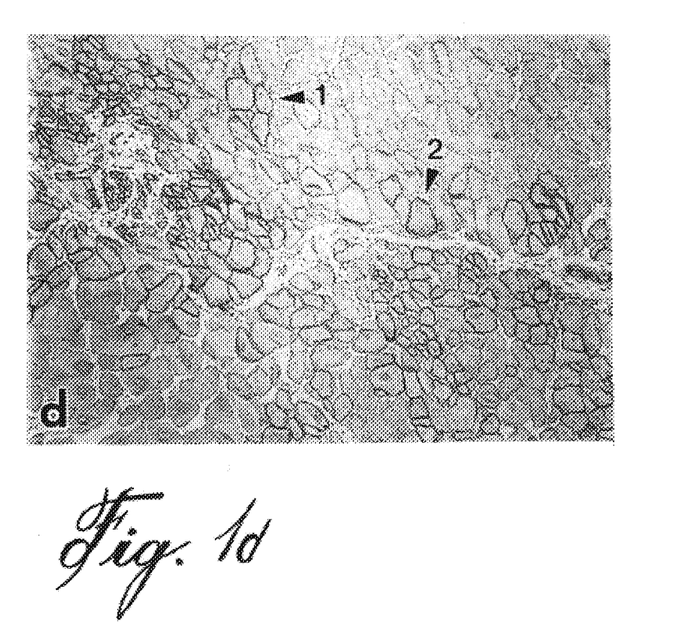
Figure 1E:
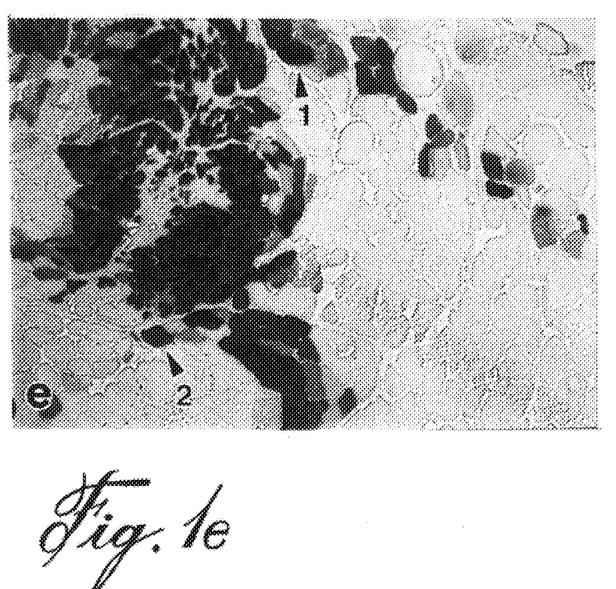
Figure 1F:
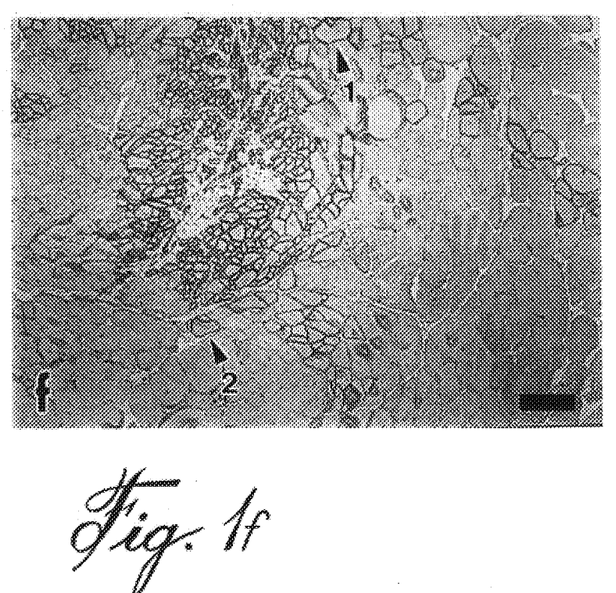

The present invention will be further described by way of the following Examples and FIG. 1, which purpose is to illustrate this invention rather than to limit its scope.

BRIEF DESCRIPTION OF FIG. 1

This FIGURE shows cross sections of TA muscle of mdx mice 28 days after injection of the transgenic myoblasts. Pairs of serial sections from 3 different muscles of three mice are illustrated. Panels a and b illustrate sections of muscles injected with myoblasts grown without bFGF. Panels c to f illustrate sections of muscles injected with myoblasts grown with bFGF. In each pair, one section was stained for β-galactosidase (panels a, c and e). The other section of the pair was immunostained for dystrophin (panels b, d and f). The muscles injected with myoblasts grown in presence of bFGF contained much more β-galactosidase and dystrophin positive fibers than muscles injected with myoblasts grown without bFGF. Most muscle fibers expressing β-galactosidase were dystrophin-positive. In each pair of panels, the same muscle fibers are identified by the same numbers. Scale bar is 100 μm.

EXAMPLE 1

Materials and Methods

Myoblast Cultures

Primary myoblast cultures were established from muscle biopsies of newborn transgenic mice[26]. The founder mouse (TnI Lac Z1/29) was provided by Dr. Hasting (McGill University, Montreal, Canada) onto the CD1 background and was reproduced in our laboratory. This transgenic mouse expresses the β-galactosidase gene under the control of the promoter of the quail fast skeletal muscle troponin I gene[16]. Blue muscle fibers are revealed in these transgenic mice following incubation with a substrate, 5-brom-4-chlor-3-indolyl-β-D-galactopyronoside (X-gal) (Boehringer Mannheim Canada, Laval, Canada). Before starting myoblast cultures, it was necessary to identify transgenic newborns by X-gal staining of a small muscle biopsy because heterozygote transgenic mice were used as parents. Myogenic cells were released from skeletal muscle fragments of the transgenic newborns by serial enzyme treatments. First, a one hour digestion was done with 600 U/ml collagenase (Sigma, St-Louis, Mo., USA). This was followed by a 30 minute incubation in Hanck's balanced salt solution (HBSS) containing 0.1% w/v trypsin (Gibco Lab, Grand Island, N.Y., USA). Satellite cells were placed in 75 cm$^2$ culture flasks (Coster, Cambridge, Mass., USA) in proliferating medium, i.e. 199 medium (Gibco Lab.) with 15% fetal bovine serum (Gibco Lab.), 1% penicillin (10,000 U/ml) and 1% streptomycin (10,000 U/ml).

Myoblast Transplantation

One day after starting culture, the culture medium of some flasks was replaced by medium containing 100 ng/ml human recombinant bFGF (Sigma). Three days after starting culture, myoblasts were detached from the flasks with 0.1% trypsin followed by three suspensions in HBSS and centrifugations (6500 RPM, 5 minutes). The final cell pellet was diluted in only 40 μl of HBSS.

Seventeen C57BL/10ScSn mdx/mdx mice (mdx mice) approximately one month old were used for this experiment. This work was authorized and supervised by the Laval University Animal Care Committee and was conducted according to the guidelines set out by the Canadian Council of Animal Care.

The mdx mice were divided in three groups. Six mdx mice of one group were grafted in both tibialis anterior (TA) muscles: myoblasts grown with bFGF were injected in the left TA and myoblasts grown without bFGF were injected in the right TA. Myoblasts grown without bFGF were injected in only the left TA of six other mdx mice. These six mdx mice were then injected intramuscularly four times (after grafting 0, +1, +4 and +6 days) either with 10 μl of bFGF (100 ng/ml, 3 mice) or with 10 μl of HBSS (3 mice). The last five mice were grafted in both TA muscle with normal CD1 mouse myoblasts infected with replication defective retroviral vector LNPOZC7 (gift from Dr C. Cepko, Harward, Boston, Mass.) which contains the LacZ gene. The left TA muscles were injected with 4 million myoblasts grown with bFGF, while the right TA muscles were injected with 4 million myoblasts grown without bFGF. Three days after grafting, these 5 mice were sacrificed to detect the number of β-galactosidase positive cells which survived in each TA muscle. The numbers of β-galactosidase positive cells were counted in 8 μm sections obtained at every 160 μm throughout the muscle. The total number of cells counted was multiplied by 20 to obtain an estimate of the number of surviving cells and a correction was made to account for the percentage of unlabelled cells in cultures with and without bFGF.

For the myoblast injection, the mice were anesthetized with 0.05 ml of a solution containing 10 mg/ml of ketamine and 10 mg/ml xylazine. The skin was opened to expose the TA muscle. The myoblast suspension was taken up into a glass micropipette with 50 μm tip (Drummond Scientific Company, Broomall, Pa., USA). The TA muscle was injected at 10 sites with a total of about 5 million cells. The skin was then closed with fine sutures. FK 506 (Fujisawa Pharmaceutical Co Ltd, Osaka, Japan) was administered at 2.5 mg/kg to immunosuppress the animals. Alternatively, the immunosuppressive treatment can be made by other pharmacological agents like cyclosporin (Sandoz), RS61443 (Syntex) or rapamycin (Wyeth-Ayerst)[42].

Muscle Examination

Three or twenty-eight days after myoblast transplantation, the mice were sacrificed by intracardiac perfusion with 0.9% saline under deep anesthesia of 10 mg/ml ketamine and 10 mg/ml xylazine. The TA muscles were taken out and immersed in a 30% sucrose solution at 4° C. for 12 hours. The specimens were embedded in OCT (Miles Inc, Elkhart, Ind. USA) and frozen in liquid nitrogen. Serial cryostat sections (8 μm) of the muscles were thawed on gelatin coated slides. These sections were fixed in 0.25% glutaraldehyde and stained in 0.4 mM X-gal in a dark box overnight (12 hours) at room temperature to detect the muscle fibers containing β-galactosidase. Dystrophin was detected on adjacent cryostat sections by an immunoperoxidase technique with a sheep polyclonal antibody against the 60 KD dystrophin fragment (R27, Genica Co, Boston, Mass., USA) and the peroxidase activity was revealed by a 10 minute incubation with 3,3' diaminobenzidine (DAB, 0.5 mg/ml, Sigma) and hydrogen peroxidase (0.015%).

Desmin Staining

The primary cultures were washed with PBS and fixed with 100% methanol at −4° C. They were then washed again 3 times with PBS and incubated 1 hr with a mAb anti-human desmin (Dako, Copenhagen, Denmark) diluted 1/50 with PBS containing 1% blocking serum (i.e. 0.33% rabbit serum, 0.33% horse serum and 0.33 fetal calf serum). They were washed 3 times with PBS with 1% blocking serum and incubated 1 hr with a 1/100 dilution (in PBS with 1% blocking serum) of a rabbit anti-mouse immunoglobulin (Dako). Following 3 washes with PBS, the peroxidase activity was revealed with DAB as for dystrophin immunohistochemistry.

Results

Myoblasts from muscle biopsies of transgenic mice expressing β-galactosidase under a muscle specific promoter were grown with or without bFGF and injected in mdx muscles not previous irradiated or damaged with notexin. A month later, the animals were sacrificed and the injected muscles were examined for the presence of β-galactosidase and dystrophin. Many positive muscle fibers were observed. In our previous experiments, muscles of mdx mice which did not receive injections of transgenic myoblasts remained completely devoid of β-galactosidase-positive fibers[22]. Therefore all β-galactosidase-positive muscle fibers observed in grafted mdx muscles are resulting from the fusion of some donor myoblasts among themselves (donor's fibers) or with the host myoblasts (hybrid fibers). In serial muscle sections, most of the β-galactosidase-positive muscle fibers were observed to be also dystrophin-positive (FIG. 1). In all biopsied TA muscles, the number of β-galactosidase-positive muscle fibers was counted and expressed as a percentage of the total number of fibers in a cross section. The sections containing of the maximum percentage of β-galactosidase-positive muscle fibers were selected for each muscle. In mdx mice grated in both TA muscles, the percentage of β-galactosidase-positive muscle fibers in the left TA muscle (grafted with myoblasts grown with bFGF) was compared with that in the right TA muscle (grafted with myoblasts grown without bFGF) of the same mouse (Table 1). Without notexin and irradiation, only a low percentage of hybrid or donor muscle fibers were observed in the right TA muscle i.e. the mean number of β-galactosidase-positive fibers per muscle cross section was 156.3 giving a mean percentage of β-galactosidase-positive fibers of 8.396. The left TA muscles contained, however, significantly more hybrid or donor muscle fibers, i.e. the mean number of β-galactosidase-positive fibers per muscle cross section was 773.7 thus giving a mean percentage of β-galactosidase-positive fibers equal to 34.4% (FIG. 1). This is more than a four fold increase in the efficacy of myoblast transplantation produced by the addition of bFGF to the culture medium.

We have also investigated whether the beneficial effect of bFGF could be obtained by injecting it directly in the muscle at 4 intervals after myoblast transplantation. No significant difference in the percentage of hybrid or donor muscle fibers (i.e. β-galactosidase positive fibers) was observed between the groups which received intramuscular injections of bFGF and those which received HBSS injections (control) (Table 2). The percentage of β-galactosidase positive muscle fibers was, however, higher following repeated injection of HBSS (14.8%) or of bFGF (15.9%) than following injection of myoblasts alone grown without bFGF (Table 1, 8.3%). This may be due to damage produced by the repeated injections which may increase the regeneration process.

It has been reported recently by Huard et al.[21] and by Beauchamp et al.[7], that a high percentage of the myoblasts injected in a muscle died within the first few days following their transplantation. To examine whether the increase efficiency of myoblast transplantation following culture with bFGF could be due to a reduced cell death, we have labelled normal CD1 primary cultures grown with or without bFGF with a retroviral vector containing the β-galactosidase gene under an LTR promoter. Normal myoblasts were labelled with a retroviral expressing β-galactosidase because only mature myoblasts and myotubes of transgenic TnI LacZ 1/29 can express β-galactosidase. With labelling using a retroviral vector a higher percentage of the cells in the primary culture expressed the reporter gene. The retrovirally labelled cells were then injected in a muscle of 5 mice. We examined the number of β-galactosidase positive cells 3 days after their transplantation. In all 5 mice, the number of the cells was not significantly higher in left TA muscles (with bFGF) ($3.29 \pm 1.54 \times 10^5$ cells) than in right TA muscles (without bFGF $2.13 \pm 0.40 \times 10^5$ cells). Note that since $4 \times 10^6$ cells were injected in each muscle, there is only 5.3% of the injected cells surviving at 3 days without bFGF while only 8.2% of the injected cells survived with bFGF.

To try to understand the beneficial effects of bFGF on myoblast transplantation, we examined the effect of a short stimulation (2 days) with 100 ng/ml bFGF on primary myoblast cultures. The total number of cells in each flask was not significant different ($31.9 \pm 6.8 \times 10^6$ with bFGF n=5, $30.0 \pm 5.8 \times 10^6$ without FGF n=9, unpaired t-test: p=0.573). The myoblasts and myotubes were then identified by revealing desmin by immunoperoxidase. In these cultures, there was no difference in the percentage of myogenic nuclei (nuclei in myoblasts and in myotubes) between the two groups of cultures (Table 3, line 1). More myogenic cells were however fused in the absence of bFGF (Table 3, line 2). There was an higher percentage of the total nuclei (including myoblasts, myotubes and fibroblasts) which were myoblast nuclei in cultures containing bFGF (Table 3 line 3). The increase of myoblasts was more clear when the percentage of myoblasts was calculated among mononuclear cells (excluding the myotubes) (Table 3, lines 4 and 5). This was however only a 35% increase.

TABLE 1

Effect of culture with or without bFGF on the formation of muscle fibers containing donor's gene in mdx mice

| No of mdx mice | no bFGF (right TA muscle) No (%) of β-gal. positive fibers | with bFGF (left TA muscle) No (%) of β-gal. positive fibers |
|---|---|---|
| 1 | 170(11.0) | 514(19.3) |
| 2 | 259(11.9) | 438(20.4) |
| 3 | 259(13.1) | 1007(37.4) |
| 4 | 57(4.1) | 695(34.0) |
| 5 | 139(6.1) | 848(43.8) |

TABLE 1-continued

Effect of culture with or without bFGF on the formation of muscle fibers containing donor's gene in mdx mice

| No of mdx mice | no bFGF (right TA muscle) No (%) of β-gal. positive fibers | with bFGF (left TA muscle) No (%) of β-gal. positive fibers |
|---|---|---|
| 6 | 54(3.6) | 1140(51.7) |
| Mean ± SD | 156.3 ± 91.5(8.3 ± 4.2)# | 773.7 ± 275.8(34.4 ± 12.8)# |

Paired t-test indicated a significant difference (p < 0.05)

TABLE 2

Effect of intramuscular injections of bFGF in mdx mice

| | No (5%) of β-gal. positive fibers | Mean ± SD |
|---|---|---|
| HBSS IM injections | | |
| 1 | 180(12.4) | 372.0 ± 172.8 (14.8 ± 2.9) |
| 2 | 421(14.1) | |
| 3 | 515(18.0) | |
| bFGF IM injections | | |
| 1 | 176(7.4) | 289.7 ± 167.5 (15.9 ± 8.4) |
| 2 | 482(24.1) | |
| 3 | 211(16.3) | T test indicated no significant difference (p > .05) |

TABLE 3

Effects of bFGF on primary myoblast culture

| | no bFGF (mean ± SD) | with bFGF (mean ± SD) | sign |
|---|---|---|---|
| 1) % of myoblast and myotube nucleic relative to total nuclei | 34.5 ± 5.3 | 35.1 ± 4.8 | 0.81 |
| 2) % of myotube nuclei relative to total myotube and myoblast nuclei | 40.8 ± 8.0 | 11.5 ± 6.6 | 0.0001 |
| 3) % myoblast nuclei relative to total nuclei | 21.1 ± 3.6 | 30.9 ± 3.8 | 0.0001 |
| 4) % myoblast nuclei relative to non myotube nuclei | 23.9 ± 5.4 | 32.2 ± 4.1 | 0.001 |
| 5) % of non-myoblast nuclei relative to non myotube nuclei | 76.1 ± 5.4 | 67.8 ± 4.1 | 0.001 |

EXAMPLE 2

The above results can be extrapolated to an in vivo utility and verified in patients suffering of muscular dystrophy. The healthy donors and DMD recipients should be matched, if possible, upon their compatibility for the MHC (HLA)-class I (A,B,C) and -class II (Dr) antigens. The dystrophic patients should undertake an immunosuppressive treatment by being administered, for example, FK 506, cyclosporin, RS61443 or rapamycin. Donors' biopsy would then be treated substantially in accordance with the procedures given in Example 1 with regard to mice myoblasts. The success of the transplantation might be monitored by measuring the incidence of dystrophin-positive fibers from a biopsy obtained from the site of transplantation and by evaluating the resulting increase of muscular strength[39].

References

1. Allen R E and Boxhorn A L: Regulation of skeletal muscle satellite cell proliferation and differentiation by transforming growth factor-beta, insulin-like growth factor 1, and fibroblast growth factor. J Cell Physiol 1989;138: 311–315.

2. Anderson J E, Kakulas B A, Jacobsen P F, Johnsen R D, Kornegay J N and Grounds M D: Comparison of basic growth factor in x-linked dystrophin-deficient myopathies of human, dog and mouse. Growth Factor 1993; 9: 107–121.

3. Anderson J E, Liu L and Kardami E: Distinctive patterns of basic fibroblast growth factor (bFGF) distribution in degenerating and regenerating areas of dystrophic (mdx) striated muscles. Develop Biol 1991;147: 96–109.

4. Austin L, Bower J, Kurek J and Vakakis N: Effect of leukaemia inhibitory factor and other cytokines on murine and human myoblast proliferation. J Neurol Sci 1992;112:185–191.

5. Austin L and Burgess A W: Stimulation of myoblast proliferation in culture by leukaemia inhibitory factor and other cytokines. J Neurol Sci 1991;101: 193–197.

6. Arahata K, Ishiura S, Tsukahara T, Suhara Y, Eguchi C, Ishihara T, Nonaka I, Ozawa E and Sugita H: Immunostaining of skeletal and cardiac muscle membrane with antibody against Duchenne muscular dystrophy peptide. Nature 1988; 333: 861–863.

7. Beauchamp J R, Morgan J E, Pagel C N, Partridge T A: Quantitative studies of the efficacy of myoblast transplantation. Muscle and Nerve Supp. 1, S261, 1994.

8. Bischoff R: A satellite cell mitogen from crushed muscle. Dev. Biol. 1986; 115:140–147.

9. Chen G and Quinn L S: Partial characterization of skeletal myoblast mitogen in mouse crushed muscle extract. J Cell Physiol 1992;153: 563–574.

10. Chen M, Li H J, Fang Q, Goodwin T G, Florendo J A and Law P K: Dystrophin cytochemistry in mdx mouse muscle injected with labeled normal myoblasts. Cell Transpl 1992;1: 17–22.

11. Clarke M S F, Khakee R and McNeil P L: Loss of cytoplasmic basic fibroblast growth factor from physiologically wounded myofibers of normal and dystrophic muscle. J Cell Sci 1993.;106: 121–133.

12. Clegg C H, Linkhart T A, Olwin B B and Hauschka S D: Growth factor control of skeletal muscle differentiation: Commitment to terminal differentiation occurs in G1 phase and repressed by fibroblast growth factor. J Cell Biol 1987; 105: 949–956.

13. DiMario J, Buffinger N, Yamada S and Strohman R C: Fibroblast growth factor in the extracellular matrix of dystrophic (mdx) mouse muscle. Science 1989; 244: 688–690.

14. DiMario J and Strohman R C: Satellite cells from dystrophic (mdx) mouse muscle are stimulated by fibroblast growth factor in vitro. Differentiation 1988; 39: 42–49.

15. Florini J R and Margri K A: Effect of growth factors on myogenic differentiation. Am J Physiol 1989; 256: C701–C711.

16. Grounds M D: Towards understanding skeletal muscle regeneration. Path Res Pract 1991;187:1–22.

17. Gussoni E, Pavlath P K, Lanctot A M, Sharma K, Miller R G, Steinman L and Blaud H M: Normal dystrophin transcripts detected in DMD patients after myoblast transplantation. Nature 1992; 356: 435–438.

18. Hallauer S M, Bradshaw H W and Hasting K E M: Complex fiber-type specific expression of fast skeletal muscle troponin I gene constructs in transgenic mice. Development 1993;119: 691–701.

19. Hoffman E P, Brown R H and Kunkel L M: Dystrophin: the protein product of Duchenne muscular dystrophy locus. Cell 1987; 51: 919–928.

20. Hsu H-Y, Nicholson A C and Hajjar D P: Basic Fibroblast Growth Factor-induced Low Density Lipoprotein Receptor Transcription and Surface Expression. J. Biol. Chem. 1994; 269: 9213–9220.

21. Huard J, Ascadi G, Jani A, Massi B: Gene transfer into mdx skeletal muscle by isogenic, genetically labelled myoblasts. Muscle and Nerve, Suppl. 1, S260, 1994.

22. Huard J, Bouchard J P, Roy R, Malouin F, Dansereau G, Labrecque C, Albert N, Richards C L, Lemieux B and Tremblay J P: Human myoblast transplantation: preliminary results of 4 cases. Muscle and Nerve 1992; 15: 550–560.

23. Huard J, Verreault S, Roy R, Tremblay M and Tremblay J P: High efficiency of muscle regeneration following human myoblast clone transplantation in SCID mice. J Clin Invest 1994; 93: 586–599.

24. Karpati G, Ajdukovic D, Arnold D, Gledhill R B, Guttmann R, Holland P, Koch P A, Shoubridge E, Spence D, Vanasse M, Watters G V, Abrahamowicz M, Duff C and Worton R G: Myoblast transfer in Duchenne muscular dystrophy. Ann Neurol 1993; 34: 8–17.

25. Karpati G, Pouliot Y, Zubrzyccka-Gaarn E, Carpenter S, Ray P N, Worton R G and Holl P: Dystrophin is expressed in mdx skeletal muscle fibers after normal myoblast implantation. Am J Pathol 1989; 135: 27–32.

26. Kinoshita I, Huard J and Tremblay J P: Utilization of myoblasts from transgenic mice to evaluate the efficacy of myoblast transplantation. Muscle and Nerve 1994;17:975–980.

27. Kinoshita I, Vilquin J P, Guerette B, Asselin I, Roy R, Tremblay J P. Very efficient myoblast allotransplantation in mice under FK506 immunosuppression. Muscle and Nerve 1994; 17: 1407–1415.

28. Koenig M, Hoffman E P, Bertelson C J, Monaco A P, Feener C and Kunkel L M: Complete cloning of the Duchenne muscular dystrophy (DMD) cDNA and preliminary genomic organization of the DMD gene in normal and affected individuals. Cell 1987; 50: 509–517.

29. Labrecque C, Roy R and Tremblay J P: Immune reaction after myoblast transplantation in mouse muscle. Transplant Proc 1992; 24: 2889–2892.

30. Law P K, Bertorini T E, Goodwin T G, Chen M, Fang Q, Kirby D S, Florendo J A, Herrod H G and Golden G S: Dystrophin production induced by myoblast transfer therapy in Duchenne muscular dystrophy. Lancet 1990; 336: 114–115.

31. Lowe W L, Yorek M A and Teasdale R M: Ligands That Activate Protein Kinase-C Differ in Their Ability to Regulate Basic Fibroblast Growth Factor and Insulin-Like Growth Factor-I Messenger Ribonucleic Acid Levels. Endocrinology 1993; 132: 1593–1602.

32. Morgan J E: Cell and gene therapy in Duchenne muscular dystrophy. Human Gene Therapy 1994; 5:165–173.

33. Morgan J E, Pagel C N, Sherratt T and Partridge T: Long-term persistence and migration of myogenic cells injected into preirradiated muscles of mdx mice. J Neurol Sci 1993;115:191–200.

34. Partridge T A: Myoblast transfer: a possible therapy for inherited myopathies? Muscle and Nerve 1991;14:197–212.

35. Partridge T A, Morgan J E, Coulton G R, Hoffman E P and Kunkel L M: Conversion of mdx myofibers from dystrophin negative to positive by injection of normal myoblasts. Nature 1989; 337: 176–179.

36. Patte C and Blanquet P R: Possible involvement of arachidonic acid metabolites in the synergistic action of endothelial mitogenesis by basic fibroblast growth factor and phorbol ester. Cell. Mol. Biol. 1992; 38: 429–436.

37. Sugita H, Arahata K, Ishiguro T, Suhara Y, Tsukahara T, Ishiura S, Eguchi C, Nonaka I and Ozawa E: Negative immunostaining of Duchenne muscular dystrophy (DMD) and mdx muscle surface membrane with antibody against synthetic peptide fragment predicated from DMD cDNA. Proc Japan Acad 1988; 64: 37–39.

38. Tremblay J P, Bouchard J P, Malouin F, Théau D, Cottrell F, Collin H, Rouche A, Gilgenkrantz S, Abbadi N, Tremblay M, Tomé F M S and Fardeau M: Myoblast transplantation between monozygotic twin girl carrier of Duchenne muscular dystrophy. Neuromusc. Disord. 1993; 3(5/6): 583–592.

39. Tremblay J P, Malouin F, Roy R, Huard J, Bouchard J P, Satoh A and Richards C L: Results of a triple blind clinical study of myoblast transplantations without immunosuppressive treatment in young boys with Duchenne muscular dystrophy. Cell Transplantation 1993; 2: 99–112.

40. Tienari J, Pertovaara L, Saksela O, Lehtonen E and Vartio T: Increased expression of the matrix metalloproteinase 2 in differentiating tera 2 human embryonal carcinoma cells. Int. J. Cancer 1994; 56: 219–223.

41. Vaidya T B, Rhodes S J, Traparowsky E J and Konieczny S F: Fibroblast growth factor and transforming growth factor β repress transcription of myogenic regulatory gene MyoD1. Molecular Cellular Biol 1989; 9: 3576–3579.

42. Vilquin J-T, Asselin I, Guérette B, Kinoshita I, Lille S, Roy R, and Tremblay J P: Myoblast Allotransplantation in Mice: Degree of Success Varies Depending on the Efficacy of Various Inmmunosupressive Treatments. Transpl. Proc. 1994; 26: 3372–3373.

43. Wakeford S, Watt D J, Partridge T A: X-irradiation improves mdx mouse muscle as a model of myofiber loss in DMD. Muscle and Nerve 1991; 14: 42–50.

What is claimed is:

1. In a method of transplantation of myoblasts into muscular tissue of a recipient individual in need of said transplantation, the improvement comprising growing said myoblasts in a culture medium comprising a muscle fusion-promoting amount of basic fibroblast growth factor (bFGF) and in the absence of Leukemia Inhibitory Factor (LIF), whereby said improvement results in an increase in the number of functional muscle cells in said recipient individual.

2. The method of claim 1, wherein said recipient individual suffers from Duchenne muscular dystrophy.

3. The method of claim 1, wherein said growing of said myoblasts comprises an in vitro preconditioning step which avoids undesirable effects associated with an in vivo preconditioning step of said recipient individual's muscular tissue by irradiation or by administering of a muscular toxin.

4. The method of claim 2, wherein said growing of donor's myoblasts comprises an in vitro preconditioning step which avoids undesirable effects associated with an in vivo preconditioning step of said recipient individual's muscular tissue by irradiation or by administering of a muscular toxin.

5. The method of claim 1, wherein said culture medium further comprises at least one growth or trophic factor selected from the group consisting of, insulin growth factor I, transferrin, platelet-derived growth factor, epidermal growth factor, adrenocorticotrophin, macrophage colony-stimulating factor, protein kinase C activators and agonists thereof.

6. The method of claim 2, wherein said culture medium further comprises at least one growth or trophic factor selected from the group consisting of, insulin growth factor I, transferrin, platelet-derived growth factor, epidermal growth factor, adrenocorticotrophin, macrophage colony-stimulating factor, protein kinase C activators and agonists thereof.

7. The method of claim 1, wherein said myoblasts consist essentially of a primary myoblast culture obtained by culturing an enzymatic cell dispersion of a muscle biopsy.

8. The method of claim 2, wherein said myoblasts consist essentially of a primary myoblast culture obtained by culturing an enzymatic cell dispersion of a muscle biopsy.

9. The method of claim 7 wherein said primary myoblast culture is grown in the presence of about 100 ng of bFGF per milliliter of culture medium for about 48 hours before transplantation.

10. The method of claim 8 wherein said primary myoblast culture is grown in the presence of about 100 ng of bFGF per milliliter of culture medium for about 48 hours before transplantation.

11. The method of claim 9 wherein said increase of the number of functional muscular cells is approximately four fold.

12. The method of claim 10 wherein said increase of the number of functional muscular cells is approximately four fold.

13. The method of claim 1, wherein said growing of said myoblasts comprises an in vitro preconditioning step which minimizes undesirable effects associated with an in vivo preconditioning step of said recipient individual's muscular tissue by irradiation or by administering of a muscular toxin.

14. The method of claim 2, wherein said growing of said myoblasts comprises an in vitro preconditioning step which minimizes undesirable effects associated with an in vivo preconditioning step of said recipient individual's muscular tissue by irradiation or by administering of a muscular toxin.

15. A method of in vitro preconditioning myoblasts prior to a transplantation thereof into a recipient individual in need of said transplantation comprising growing said myoblasts in a culture medium comprising a muscle fusion-promoting amount of basic fibroblast growth factor (bFGF) and in the absence of Leukemia Inhibitory Factor (LIF), whereby said preconditioning enhances the success of the transplantation by increasing the number of functional muscle cells in said recipient individual.

16. The method of claim 15, wherein said recipient individual in need of said transplantation suffers from Duchenne muscular dystrophy.

17. The method of claim 16, wherein said in vitro preconditioning further comprises an incubation of said myoblasts of said donor with at least one growth or trophic factor selected from the group consisting of, insulin growth factor I, transferrin, platelet-derived growth factor, epidermal growth factor, adrenocorticotrophin, macrophage colony-stimulating factor, protein kinase C activators and agonists thereof.

18. The method of claim 15, wherein said recipient suffers from a recessive myopathy.

19. The method of claim 15, wherein said recipient is undertaking immunosuppressive therapy.

20. The method of claim 16, wherein said bFGF is human bFGF.

21. A method of myoblast transplantation comprising contacting myoblasts from a donor with a muscle fusion-promoting amount of basic fibroblast growth factor (bFGF) and in the absence of Leukaemia Inhibitory Factor (LIF) for a time and under conditions sufficient to obtain preconditioned myoblasts and administering said preconditioned myoblasts into a recipient individual, whereby said preconditioned myoblasts increase the number of hybrid muscle fibers in said recipient.

22. The method of claim 21, which further comprises the contacting of said myoblasts from a donor with at least one factor selected from the group consisting of insulin growth factor I, transferrin, platelet-derived growth factor, epidermal growth factor, adrenocorticotrophin, macrophage colony-stimulating factor, protein kinase C activators and agonists thereof.

23. The method of claim 21, wherein said donor and said recipient are compatible.

24. The method of claim 21, wherein bFGF is provided at a concentration of about 100 mg per milliliter.

25. The method of claim 24, wherein bFGF is human bFGF.

26. A method of improving the fusion of myoblasts upon transplantation thereof into muscular tissue of a recipient individual comprising growing said myoblasts in a culture medium comprising a muscle fusion-promoting amount of basic fibroblast growth factor (bFGF) and in the absence of Leukaemia Inhibitory Factor (LIF).

27. The method of claim 26, wherein said culture medium further comprises at least one growth factor or trophic factor selected from the group consisting of insulin growth factor I, transferrin, platelet-derived growth factor, epidermal growth factor, adrenocorticotrophin, macrophage colony-stimulating factor, protein kinase C activators and agonists thereof.

28. A method of increasing the number of hybrid muscle fibers in a recipient individual upon myoblast transplantation comprising growing said myoblasts in a culture medium comprising a muscle fusion-promoting amount of basic fibroblast growth factor (bFGF) and in the absence of Leukaemia Inhibitory Factor (LIF) prior the myoblast transplantation.

29. The method of claim 28, wherein said culture medium further comprises at least one growth factor or trophic factor selected from the group consisting of insulin growth factor I, transferrin, platelet-derived growth factor, epidermal growth factor, adrenocorticotrophin, macrophage colony-stimulating factor, protein kinase C activators and agonists thereof.

* * * * *